US005804405A

United States Patent [19]

Ahlfors

[11] Patent Number: 5,804,405
[45] Date of Patent: Sep. 8, 1998

[54] BILIRUBIN DETECTION

[75] Inventor: Charles E. Ahlfors, San Francisco, Calif.

[73] Assignee: Research Corporation Technologies, Inc., Tucson, Ariz.

[21] Appl. No.: 757,930

[22] Filed: Nov. 27, 1996

[51] Int. Cl.$^6$ .............................. C12Q 1/28; C12Q 1/26; C12Q 1/00; G01N 33/53
[52] U.S. Cl. ................................ 435/28; 435/25; 435/4; 435/975; 436/66; 436/63; 436/68; 436/97; 562/58; 422/50; 422/68.1; 422/61; 422/62
[58] Field of Search .................................. 435/28, 25, 4, 435/975; 436/66, 63, 68, 97; 562/58; 422/50, 68.1, 61, 62

[56] References Cited

U.S. PATENT DOCUMENTS

| | | | |
|---|---|---|---|
| 3,652,222 | 3/1972 | Denney et al. | 435/28 |
| 4,311,483 | 1/1982 | Perry | 435/28 |
| 4,311,665 | 1/1982 | Wu | 435/28 |
| 4,338,095 | 7/1982 | Wu | 435/28 |
| 4,376,828 | 3/1983 | Rupchock et al. | 435/28 |
| 4,404,286 | 9/1983 | Shull | 435/28 |
| 4,563,429 | 1/1986 | Doumas et al. | 435/28 |
| 4,672,041 | 6/1987 | Jain | 435/28 |
| 5,104,794 | 4/1992 | Kondo et al. | 435/28 |

FOREIGN PATENT DOCUMENTS 0 024 112   2/1981   European Pat. Off. .

OTHER PUBLICATIONS

Ahlfors, "Effect of Serum Dilution on Apparent Unbound Bilirubin Concentration as Measured by the Peroxidase Method", Clinical Chemistry, vol. 27, No. 5, 1981, pp. 692–696.

Jacobsen, et al. "Determination of Unbound Bilirubin he Serum of Newborns", Clinical Chemistry, vol. 20, No. 7, 1974, pp. 783–789.

Labrune, et al. "Gunn rats: a reproducible experimental model to compare the different methods of measurements of bilirubin serum concentration . . . ", Clinicia Chimica Acta, 192, 1990, pp. 29–34.

Wells et al. "Relationships of Bilirubin Binding Parameters", Clinical Chem, Vol. 28, No. 3, 1982, pp. 432–439.

International Search Report of PCT Application PCT/US97/21275.

Ahlfors, C.E., (1994) "Criteria for Exchange Transfusion in Jaundiced Newborns,"*Pediatrics* 93 (3):488–494.

Ahlfors, C.E., !1981) "Competitive interaction of biliverdin and bilirubin only at the primary bilirubin binding site on human albumin,"*Analytical Biochem.* 110:295–307.

Broderson et al., (1969) "Enzymatic Oxidation of Bilirubin," *Eur. J. Biochem* 10:468–473.

Cornish–Bowden A., Eisenthal R., (1978) "Estimation of Michaelis constant and maximum velocity from the direct linear plot," *Biochem. Biophys Acta* 523:268–272.

Good, N.E, (1966) "Hydrogen ion buffers for biological research," *Biochem* 5 (2):467–477.

Henry, R. et al., (1974) *Clinical Chemistry, Principles and Techniques* 2d, Ed., Harper and Row, N.Y., N.Y., pp. 1037–1079.

Jacobsen, J. et al., (1974) "Determination of Unbound Bilirubin in the Serum of Newborns,"*Clinical Chem* 20(7):783–789.

Jendrassik, L. and Grof, P. (1938) "Vereinfachte Photometrische Methoden zur Bestimmung des Blutbilirubins," *Biochem. Z.* 297:81–89.

Lillie, H. J. (1969) "Diazonium and Tetrazonium Salts, " *Conn's Biological Stains*, Williams & Wilkins Company, Baltimore, MA, Chap. VI, pp. 128–153.

Martinek, R., (1966) "Improved Micro–method for Determination of Serum Bilirubin,"*Clin. Chim. Acta* 13:161–170.

Shimabuku et al., (1982) "Total and Unbound Bilirubin Determination Using an Automated Peroxidase Micromethod," *Kobe J. Med. Sci* 28:91–104.

Silverman et al., (1956) "A Difference in Mortality Rate and Incidence of Kernicterus Among Premature Infants Allotted to Two Prophylactic Antibacterial Regimens," *Pediatrics* 18:614–625.

Walters and Gerarde (1970) "An Ultramicromethod for the Determination of Conjugated and Total Bilirubin in Serum or Plasma," *Microchem. J.* 15:231–243.

*Primary Examiner*—Louise N. Leary
*Attorney, Agent, or Firm*—Scully, Scott, Murphy & Presser

[57] ABSTRACT

A method is taught by which a sample can be analyzed for the selective determination of the total concentration of bilirubin ($B_t$), the concentration of conjugated bilirubin ($B_c$), the concentration of unconjugated bilirubin ($B_u$), the concentration of unbound bilirubin (b), the concentration of unbound, unconjugated bilirubin ($b_u$) using a unique combination of enzymatic and colorimetric methods in a single assay, so that the potentially neurotoxic, non-albumin bound, unconjugated fraction of total bilirubin in the sample (i.e., $b_u$) can be measured in a simple, quick and accurate manner. A kit utilizing the same assay is also described. Both kit and methods will be of use to the clinician and general researcher. The $B_t$, $B^c$, $B_u$, b and $b_u$ are determined using spectra, absorption or emission characteristics in combination with kinetic measurements of rates of reaction of chemical processes.

20 Claims, No Drawings

BILIRUBIN DETECTION

FIELD OF THE INVENTION

This invention relates generally to the area of the detection of bilirubin. More particularly it relates to a method for measuring the concentration of unconjugated bilirubin which is non-albumin bound in a sample. The instant technology can also be used in the diagnosis and treatment of hyperbilirubinemia.

BACKGROUND OF THE INVENTION

Bilirubin is bile pigment which is a metabolic product of heme formed from the degradation of erythrocytes by reticuloendothelial cells. It can also be formed by the breakdown of other heme-containing proteins such as cytochromes. The typical biological form of bilirubin is designated bilirubin IXα. Bilirubin IXα normally circulates in the plasma component of the bloodstream and is designated as "unconjugated" bilirubin. Unconjugated bilirubin may complex to serum albumin and as such is designated as "bound" unconjugated bilirubin or it may be albumin free and therefore, designated as "unbound" unconjugated bilirubin.

Both bound and unbound unconjugated bilirubin are normally transported to the liver, taken up by liver cells and converted to a polar conjugate form. The conversion typically involves the transfer of glucuronic acid molecules, catalyzed by the enzyme hepatic glucuronyl transferase, to the unconjugated bilirubin. Conjugated bilirubin, like unconjugated bilirubin, can bind to albumin, although the unconjugated form seems to bind to albumin more tightly. Thus, four distinct species of bilirubin can compose the total amount of bilirubin products found in blood, sera or tissues. They are: (1) bound conjugated bilirubin, (2) unbound conjugated bilirubin, (3) bound unconjugated bilirubin, and (4) unbound unconjugated bilirubin.

Unconjugated but not conjugated bilirubin can poison many vital cell functions and a variety of experimental and clinical evidence suggests that unbound unconjugated bilirubin is a potential neurotoxin. Specifically, unbound unconjugated bilirubin can act as a neurotoxin because of its ability to migrate from the vascular blood space into the nervous system where it can complex with nervous tissue causing irreversible damage. Typically, unbound, unconjugated bilirubin comprises less than 0.05% of the fraction of total bilirubin in the blood and is therefore difficult to measure. Disease states resulting in elevated levels of serum bilirubin may raise either "conjugated" or "unconjugated" levels of bilirubin or both forms simultaneously. However, only elevated unconjugated forms predispose a patient to bilirubin toxicity.

Newborn infants suffering from high levels of unconjugated bilirubin (i.e., hyperbilirubinemia) become jaundiced after birth and susceptible to developing kernicterus, which is an accumulation of unconjugated bilirubin in tissues of the nervous system, particularly the developing brain. This condition, also designated as bilirubin encephalopathy, may produce athetoid cerebral palsy, ocular palsy, deafness, mental retardation, and defects in fine motor control and cognitive function. Neonates afflicted with hemolysis and infants born prematurely compose the highest risk groups for bilirubin encephalopathy; however, kernicterus has also been reported in jaundiced term newborns with no clear pathological etiology for their jaundice.

Approximately 40,000 to 80,000 newborns per year in the United States are readmitted to hospital for hyperbilirubinemia. One current form of treatment for newborns with elevated levels of bilirubin in the blood is exchange transfusion. However, exchange transfusion is usually based on total blood bilirubin levels because unbound, unconjugated bilirubin is not easily measured. Exchange transfusion is associated with a significant risk of morbidity and mortality. Furthermore, since the concentration of total bilirubin in the blood correlates poorly with the risk of developing kernicterus, exchange transfusion treatments may be performed unnecessarily upon neonates who do not need the treatment. Conversely, the exchange transfusion treatment may be withheld from those infants who require it.

At present, results from either of two types of medical diagnostic tests designed to measure unbound bilirubin are used in the determination of the need for treatment by exchange transfusion. One test is based upon detecting levels of substances which are believed to correlate significantly with levels of unbound unconjugated bilirubin in the patient. For example, several methods depend upon measuring circulating levels of albumin binding sites unoccupied by bilirubin (i.e., unbound albumin). Since albumin binds with unbound unconjugated bilirubin, it has been suggested that knowledge concerning the level of unbound albumin correlates well with the amount of unbound unconjugated bilirubin in a patient. However, it is possible that such correlations do not accurately reflect the "true" level of unbound unconjugated bilirubin in the patient because a single albumin molecule can bind more than one bilirubin molecule.

A second test for hyperbilirubinemia attempts to measure the actual concentration of unbound bilirubin in the blood. This second type of test method is preferred to tests using correlative methods since a test which directly measures the species of bilirubin in a sample typically exhibits a smaller margin of error. However, currently, such assays cannot measure the fraction of the total amount of all species of bilirubin which is the neurotoxic fraction in the blood—i.e., the unbound, unconjugated bilirubin fraction.

Presently, non-correlative bilirubin assays are of two types. The first type measures total bilirubin concentration in the blood, which consists of all four species of bilirubin (i.e., (1) bound conjugated bilirubin, (2) unbound conjugated bilirubin, (3) bound unconjugated bilirubin, and (4) unbound unconjugated bilirubin). The second type measures the total bilirubin and the fraction of the total bilirubin that is conjugated. The difference between the total and conjugated bilirubin is the concentration contributed by unconjugated bilirubin. However, even this combined data still does not provide the clinician with information about the unconjugated unbound bilirubin fraction of a sample because it does not distinguish between the two types of unconjugated bilirubin—that which is bound to albumin and that which is unbound to albumin. Knowledge of the concentration of unconjugated bilirubin which is unbound to albumin (and therefore potentially toxic) is useful information.

Accordingly, a diagnostic test indicating unconjugated, unbound bilirubin would be preferred since it could specifically and accurately determine the neurotoxic fraction of total bilirubin. Knowledge of the concentration of unbound unconjugated bilirubin would be advantageous since its concentration may increase exponentially with any linear increase in the concentration of total bilirubin due to the effect of mass action on the binding of bilirubin with albumin. Therefore, an accurate measure of any change in the concentration of unbound, unconjugated bilirubin is desired because this species of bilirubin is extremely relevant in the clinical decision to administer the potential lifesaving but dangerous treatment of exchange transfusion.

A current kinetic technique for direct measurement of non-albumin bound bilirubin employs the horseradish peroxidase catalyzed oxidation of species of bilirubin by peroxide (Jacobsen & Wennberg; 1974). In this method, since only non-albumin bound bilirubin reacts with the peroxide, the reaction velocity of the oxidation of both conjugated and unconjugated bilirubin species is proportional to the concentration of non-albumin bound bilirubin within the sample. After measuring the rate constant ($K_p$) of the oxidation of bilirubin in albumin free solutions, the concentration of unbound bilirubin is determined from the rate of oxidation in the sample. However, the unbound bilirubin measured consists of both conjugated and unconjugated species of bilirubin, while it is currently believed that only the unbound, unconjugated species of bilirubin is toxic. Therefore, a method which determines the concentration of unbound, unconjugated bilirubin would be advantageous.

SUMMARY OF THE INVENTION

A method is described for directly determining the concentration of unbound, unconjugated bilirubin in a sample combining a specific sequence of kinetic and colorimetric techniques. The kinetic technique uses at least two different rates of bilirubin oxidization to determine whether the rate of dissociation of bilirubin from its complex with albumin is the limiting step in the oxidation of bilirubin. The kinetic technique also uses a reagent which terminates the enzymatic portion of the kinetic technique and can function in the colorimetric portion of the method. A sample volume of as little as 10 μl (i.e., 0.01 ml) and diluted less than 1:3 is sufficient to perform the instant assay. The method also includes a kit. Additionally a method, a system and a computer program that can be implemented in a programable computer are taught for automatically determining the concentration of unbound, unconjugated bilirubin in a sample.

DESCRIPTION OF THE INVENTION

The instant invention is shown and described herein in what is considered to be the most practical and preferred embodiments. It is recognized, however, that departures may be made from these embodiments which are within the scope of the invention and that modifications will occur to one of ordinary skill in the art upon reading this disclosure. Throughout this description, the preferred embodiment and examples shown should be considered as exemplars, rather than as limitations on the present invention. Accordingly, it is to be understood that the invention is not to be limited by the specific illustrated embodiment, but only by the scope of the appended claims.

The invention is a method which directly determines the concentration of the potentially neurotoxic components of total bilirubin present in a sample—i.e., unbound, unconjugated bilirubin. This method overcomes limitations imposed by large sample volumes or large dilutions, costly equipment or training, and extended processing delays. The method is inexpensive, fast, and extremely accurate and can be performed on standard clinical laboratory instruments capable of measuring either total or total and conjugated bilirubin concentrations.

The instant invention is useful in that it accurately measures the concentration of unbound, unconjugated bilirubin in a sample. Moreover, the instant technology determines the concentration of unbound unconjugated bilirubin in small samples with little dilution of the sample size. Often, increased dilution of a sample to perform colorimetric analysis promotes distortion resulting in inaccurate measurements of unbound bilirubin. Applicants' technology alleviates the necessity for large dilutions. Additionally, since the applicant employs standard colorimetric and kinetic enzymatic reactions, the instant methods are readily adaptable to clinical laboratories since these two techniques (i.e., kinetic and colorimetric techniques) are standard in the art and widely practiced among those of ordinary skill. Furthermore, Applicant's invention is inexpensive and does not require the purchase of expensive and sophisticated equipment.

Advantages of the instant method of determining the concentration of unbound, unconjugated bilirubin in a sample are: (1) Combining colorimetric and kinetic (i.e., enzymatic) techniques in a single method thus permitting a direct method for determining the concentration of unbound, unconjugated bilirubin in a sample; (2) small sample volumes (i.e., 10 μl or more) thus avoiding larger sample volumes which can be a limiting factor when performing laboratory tests on newborns; (3) small sample dilutions thus avoiding any masking effect of weakly binding drugs or endogenous bilirubin binding competitors in samples using large dilutions (i.e., in the range of about 1:40). Sample dilutions in the range of about 1:40 may alter bilirubinalbumin albumin binding especially if weak bilirubin binding competitors are present in the sample. The masking effect due to large sample dilutions can ultimately lead to an underestimation of the concentration of unbound unconjugated—i.e., the toxic fraction—of bilirubin; (4) the instant method measures unbound, unconjugated bilirubin directly instead of measuring the capacity of albumin to bind bilirubin by measuring the unoccupied bilirubin binding sites on the albumin molecule. The instant method of determining the concentrations of species of bilirubin does not lead to nonspecific endpoints in measurement because the instant methods do not assume that albumin binds a single bilirubin molecule but the instant methods take into consideration that albumin is capable of binding several bilirubin molecules; (5) the present technology determines each species of the fraction of bilirubin which makes up the total concentration of bilirubin in a sample, thus, permitting establishment of accurate standardized reference values or permitting a strategy for establishing reference values useful during clinical treatment of bilirubin disease states; (6) the present technology uses reaction conditions that eliminate or correct for the potential rate limiting dissociation of bilirubin from albumin since, if the rate of dissociation of bilirubin from its complex with albumin is the rate limiting step in the oxidation of bilirubin, the unbound bilirubin concentration can be significantly underestimated; (7) the present technology corrects for any errors in measurement due to the oxidation of conjugated bilirubin in the sample as opposed to measuring both conjugated and unconjugated unbound bilirubin since both species can be oxidized yet only the unconjugated unbound is potentially toxic. Therefore, the conflating effect of measurements of the oxidation of both conjugated and unconjugated bilirubin are eliminated by the present technology; (8) the present technology eliminates error caused by interference from conjugated bilirubin which can lead to an overestimation of the unbound unconjugated bilirubin concentration; (9) the present technology permits the use of a variety of test temperatures by teaching the temperature dependent standardization of the bilirubin oxidizing reagent and how reference values can be adjusted for the temperature selected; (10) expensive equipment is not required nor is time-consuming data processing; (11) technicians may be easily trained or instructed in performing the instant methods instead of requiring dedicated technician support and instrumentation to monitor change in bilirubin concentration over periods of time.

The instant method also provides corrections for potential error by interference from that fraction of the sample consisting of conjugated bilirubin if the instrumentation employed is capable of measuring conjugated bilirubin. Additionally, a kit composed of the reagents necessary for this method can be created from stable and inexpensive reagents. After using the instant methods reference values for levels of bilirubin can be established and employed as an adjunct in clinical treatment decisions. The details of the preferred embodiment of the present invention are set forth in the accompanying drawings and the description below. Once the details of the invention are known, numerous additional innovations and changes will become obvious to one skilled in the art.

Combination of Colorimetric and Kinetic Methods for Measuring Concentrations

The assay method of the instant invention can provide several different bilirubin assay values. For example, this method can directly determine the presence and/or concentration of unconjugated bilirubin (Br), or the presence and/or concentration of conjugated bilirubin (Bc), or the presence and/or concentration of unconjugated unbound bilirubin (b), or the presence and/or concentration of bound bilirubin (B), or the presence and/or concentration of each of the four possible combinations of conjugated or unconjugated bilirubin which is either bound or unbound to albumin, and the method can also determine the presence and/or concentration of total bilirubin ($B_T$). The method of the instant invention uniquely combines certain elements of both colorimetric techniques for measuring conjugated and unconjugated bilirubin with kinetic techniques for measuring unbound bilirubin that are known in the art.

An aspect of the invention involves employing a reagent used in a colorimetric technique which can also denature a bilirubin oxidizing reagent, such as horseradish peroxidase, thus functioning in the kinetic method by stopping the enzymatic reaction. This dual function permits the enzymatic reaction of the kinetic technique to be stopped after a set time with a reagent that can be used to determine the total and conjugated bilirubin of the method by employing a colorimetric technique. Since the conjugated fraction of bilirubin in the sample can be measured and a correction applied, any error from conjugated bilirubin can be eliminated if concentrations of conjugated bilirubin in the sample are elevated. Finally, a minimally diluted sample is used and reaction conditions for bilirubin oxidation are employed to eliminate error caused by rate limiting dissociation of bilirubin from albumin. These methods are further described herein to permit greater understanding of the instant invention.

The Colorimetric Method

A number of standard methods of assaying or quantitatively measuring bilirubin in the art are based upon colorimetric methods, which is either measuring the inherent absorbance of the bilirubin pigment itself or by mixing bilirubin in the presence of certain reagents to form a colored reaction product which is then subjected to a spectral analysis. Typically, only the total amount of bilirubin present can be determined from measuring the absorbance of the bilirubin pigment itself because the differences in the absorbance spectra of conjugated and unconjugated bilirubin are too subtle to differentiate. Therefore, many colorimetric assays for bilirubin commonly use diazotized sulfanilic acid or other diazotized reagents to form colored azobilirubin reaction products. Malloy-Evelyn; J.Biol. Chem., 119 (1937); Jendrassik-Grof, Biochem. Z., 297, 81(1938) and Walters and Gerarde; Microchem. J., 15, 231 (1970).

In diazo methods the concentration of both conjugated and unconjugated bilirubin can be determined. Conjugated bilirubin reacts with a diazo reagent before adding a subsequent reagent (e.g., methanol, caffeine, sodium benzoate, or surfactants). Once these agents are added, the unconjugated bilirubin reacts with the diazo reagent and the total bilirubin in the sample (i.e., conjugated+unconjugated) can be determined by spectral analysis of the final absorbance. The unconjugated bilirubin can then be calculated as the difference between the value of the total bilirubin and the conjugated bilirubin which have been measured in the sample.

Diazo reactions are typically carried out in the range of about between pH 1 and pH 2 to enhance the absorbance of the derivatives. At such a range of pH, horseradish peroxidase, which catalyzes the oxidation reaction of unbound species of bilirubin, is denatured. Bilirubin oxidation products, peroxides, and peroxidases do not react with diazo reagents. Therefore, if bilirubin is oxidized in a sample for a given time after which a diazo reagent is added, the oxidation reaction is terminated, and the remaining concentration of total bilirubin and the concentration of conjugated bilirubin can be measured. If the concentration of total bilirubin and the concentration of conjugated bilirubin are determined before and a set time after the initiation of the oxidation of bilirubin in the sample, these measurements can be subsequently used to calculate the concentration of unbound, unconjugated bilirubin.

To aid in maintaining the pH within the stated range these bilirubin determinations can be carried out in the presence of a buffer. Various buffers may be employed in using the methods of the instant invention such as those described by Good in Biochemistry, 5,467 (1996). However, one of ordinary skill in the art can vary the pH and temperature herein to values above or below the stated ranges depending upon the particular conditions, provided, that one does not use a pH or temperature which causes undesired side reactions or significant degradation of any bilirubin composition.

It will be appreciated by those of ordinary skill in the art that other reagents which function in an acceptable manner may be substituted for those described herein. For example, other buffers may be employed if they provide the desired pH range. The reagents used in the method of the present invention may be conveniently supplied in the form of a kit along with the necessary container and instructions.

The Kinetic Method

The kinetic method used in the instant invention operates by measuring the rates of reaction of various compositions in a chemical reaction to directly determine the concentration of various bilirubin species in a sample. Specifically, the kinetic technique portion of the method measures the rate of oxidation of unbound bilirubin by a bilirubin oxidizing reagent which oxidizes unbound bilirubin but not bound bilirubin. Additionally, the kinetic technique requires, by employing at least two different bilirubin oxidizing conditions, that a slower rate of dissociation of a bilirubin-albumin complex than the rate of bilirubin oxidatoin will not result in an underestimation of the unbound bilirubin.

Both conjugated and unconjugated bilirubin are oxidized by oxidizing reagents (e.g., peroxide) in the presence of a catalyzing reagent (e.g., a peroxidase) to diazo negative reaction products that do not absorb light in the spectral region where native bilirubin absorbs light and which are diazo negative. However, albumin binding of bilirubin prevents the oxidation of bilirubin and only unbound bilirubin can be oxidized. The kinetic technique of the instant invention makes use of these facts by "standardizing" the peroxidase catalyzed oxidation of bilirubin in the absence of albumin to determine the first order rate constant ($K_p$) from the change in the bilirubin concentration over time (i.e., the decline in the absorbance of bilirubin colored compositions over time) (Jacobsen & Wennberg; 1974). If B is the bilirubin concentration at any time, HRP the horseradish peroxidase concentration, $B_o$ the initial bilirubin concentration, and $B_f$ the bilirubin concentration at time t:

$$\frac{dB}{dt} = Kp \cdot \text{HRP} \cdot B$$

Integrating between time=zero and time=t, $$K_p = \frac{\left(\log \frac{B_f}{B_o}\right)}{\text{HRP} \cdot t}$$

The $K_p$ of solutions of HRP (100 µg/ml) prepared in 0.055M Sörensen's phosphate buffer at pH 7.4 remain stable for approximately one month when stored at 2°–4° C.

When the $K_p$ is known, the unbound, unconjugated bilirubin in a sample is determined as follows:

The total concentration of unconjugated bilirubin is determined ( the total bilirubin-conjugated bilirubin) by standard diazo technique. The actual unconjugated bilirubin in the oxidation reaction ($B_r$) is then calculated from the total unconjugated bilirubin by dividing by the dilution of the sample due to the addition of HRP and peroxide. The bilirubin of the sample is then oxidized by standardized HRP and peroxide for a specified time. At this time, a diazo reagent is added to a) stop the reaction at time t, and b) determine the remaining unconjugated bilirubin ($B_f$) from the conjugated and total bilirubin concentration at time (t). The unbound unconjugated bilirubin (b) can be calculated from the following equation:

$$b = \frac{B_r\left(\log \frac{B_f}{B_r}\right)}{K_p \cdot \text{HRP} \cdot t} \quad (1)$$

where $B_r$ is the concentration of unconjugated bilirubin in micromoles (µM) in the reaction (i.e., after dilution of the sample by the added reagents for the kinetic part of the method). HRP is typically measured in units of micrograms per milliliter (µg/ml) and the $K_p$ units are per minute per µg/ml HRP.

The temperature at which the kinetic portion of the instant method is done is critical because the reaction velocities of the kinetic technique of the method are temperature dependent. However, standardization of the bilirubin oxidizing reagent (e.g., HRP) can be performed at a variety of temperatures as long as the sample analyses are performed at the same temperatures. A preferable temperature is 21° C. (at which the $K_p$ is in the range of about eight per minute per µg/ml HRP), a more preferable temperature is 37° C. (at which the Kp is in the range of about 18 per minute per µg/ml HRP), however temperatures can be used in the range of about 19° C.–37° C. as long as the samples are analyzed at selected temperatures and any reference values are adjusted for the selected temperature.

DESCRIPTION OF THE PREFERRED EMBODIMENTS

Before the present method of determining the presence and/or concentration of the various proportions of bilirubin species, which make up the total bilirubin concentration in biological samples, are described; it is to be understood that this invention is not limited to particular methods described, as such methods, may, of course, vary. It is also to be understood that the terminology used herein is for the purpose of describing particular embodiments only, and is not intended to be limiting, since the scope of the present invention is limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety including any figures, drawings, graphs, equations or any additional explanatory material to disclose and describe the methods and/or materials in connection with which the publications are cited.

The term "conjugated" as used herein refers to the biological form of bilirubin IX α after transformation in the liver where it is converted to a polar conjugate form such as, but not limited to, a water-soluble bilirubin diglucuronide. The term "unconjugated" as used herein refers to the lipid soluble form of bilirubin designated as the isoform bilirubin IX α. The term "bound" as used herein refers to the form of bilirubin, either conjugated or unconjugated, which is complexed with albumin. The term "unbound" as used herein refers to the form of bilirubin, either conjugated or unconjugated, which is not complexed with or bound to albumin.

The term "assay" is used to mean any test undertaken to produce a measurement. In general, the term refers to any clinical chemical test as is commonly understood by those in the art. The term "directly determining" is used to mean any assay technique which measures or calculates from measurements of the actual concentration of any species of bilirubin in a sample as opposed to any assay technique that uses a measure of any non-bilirubin substance, compound, composition or molecule other than one comprising bilirubin to correlate with a presumed concentration of any species of bilirubin in a sample. The method of directly determining as used herein can be used to also determine: (a) a total concentration of bilirubin; (b) a concentration for each of the following species of bilirubin that can make up the total concentration of bilirubin: conjugated, unconjugated, bound, and unbound or any combination thereof; (c) a rate of reaction of the oxidation of bilirubin; (d) a correction for any non-peroxidase associated reactions; (e) an association-dissociation constant for bilirubin-albumin binding; (f) a correction for the rate limiting dissociation of bilirubin from albumin; (g) a rate of reaction of the background of the sample; and (h) a correction for the presence of conjugated bilirubin in the sample.

The term "species" as used herein refers to any one of the particular forms of bilirubin in a sample such as, but not restricted to, unbound bilirubin, bound bilirubin, unconjugated bilirubin, conjugated bilirubin or any combination thereof; such as unbound, unconjugated bilirubin; bound, unconjugated bilirubin; unbound, conjugated bilirubin; or bound, unconjugated bilirubin.

The term "kinetic" as used herein refers to assay techniques or methods in which the rate of a chemical reaction or parts thereof is used to determine the concentrations of some or all of the constituents of a chemical reaction. The kinetic technique comprises using a reagent that will oxidize unbound but not bound bilirubin (i.e., a bilirubin oxidizing reagent, e.g., a peroxide) in the presence of a reagent which catalyzes the oxidation reaction (i.e., a bilirubin catalyzing reagent, e.g., a peroxidase). The term "colorimetric" used herein refers to assay techniques in which a colored reaction product is formed by a chemical reaction and has unique absorption or emission characteristics which can be measured by spectral analysis. An example of a spectral analyzer is a spectrophotometer. Spectral analysis can be carried out using a variety of techniques of spectral measurements which are common to those in the art. The term "spectral analyzer" as used herein refers to any method of measuring the absorbance of a sample such as, but not restricted to, a spectrophotometer. The term "absorbance" as used herein refers to the common logarithm of the reciprocal of the transmittance of a pure solvent; also known as absorbency.

The method of spectral analysis of the instant invention can be carried out using any method known in the art such as using absorption photometry, e.g., colorimetric detection, or emission photometry, e.g., fluorimetric detection, as an appropriate mode of radiometric detection. The radiometric detection of the absorption or emission bands characteristic of the bilirubin components of the methods taught herein can be carried out using any of a variety of well-known absorption or emission detection devices and techniques commonly referred to herein as a spectral analyzer. The detection of these spectral bands can be carried out at a predetermined time after the sample is processed so that the resultant spectral data can be readily correlated to, for example, a calibration curve based on the spectral data obtained from a series of controls containing known amounts of each species of bilirubin as determined at the same or a related predetermined time interval. Additionally, to avoid spectral interference from potential interferents which may be present in the assay sample, (e.g., hemoglobin) any of the noted absorption maxima referred to herein can be detected, "off-peak." By the term "off-peak" is meant that generally spectral detection can be carried out at wavelengths about up to 20 nm from the maxima values referred to herein. Thus, as used herein, detecting a wavelength "at or near" an absorption maximum signifies at the peak wavelength ±20 nm and at an intensity no less than 50% of peak intensity. A radiometric assay as described herein is any assay based upon the detection of either emission or absorption spectral wavelengths.

The term "combining" as used herein with reference to kinetic and colorimetric techniques or assays refer to the association within a single assay of aspects of a kinetic technique and aspects of a colorimetric technique. The term "sequence" as used herein refers to the progression in which steps of an assay or technique are carried out. The term "order" as used herein refers to the sequence of performing the chain of procedures of the techniques of the method of the instant invention. Specifically, a preferable order of performing the method of the instant invention is to perform the kinetic technique prior to performing the colorimetric technique. The term "reagent" as used herein refers to a composition. The term "enzymatic" as used herein refers to a catalytic protein which mediates and promotes a chemical reaction.

The term "necessary conditions" as used herein refers to chemical conditions which are realized after successful completion of the proper order of the procedures of the instant method. Unless the necessary conditions are satisfactorily, completed subsequent chemical reactions will not proceed correctly. The term "sample" as used herein refers to a collection of fluid from a subject. The fluid can include, but is not restricted to, blood, plasma, serum, cerebrospinal fluid, sputum, tears, urine, secretions, ventricular fluid, mucous, fluids obtained from cells, tissues, organs, swabs, swipes or any other clinical method of obtaining a sample. The sample described herein preferably comes from an animal, more preferably from a human animal. Bilirubin containing fluids which can be assayed by the procedure of the instant invention include, but are not limited to, bilirubin containing blood serum or plasma, cerebrospinal fluid, amniotic fluid, and lymphatic fluid. The biological fluid to be assayed can be obtained from any mammal such as dogs, cats, rats, mice, horses, ungulates or humans. Of particular interest as a bilirubin containing biological fluid for assay is human blood serum or plasma. The use of fresh serum or plasma, which has been protected from light, is advisable to prevent decreased values due to photo-oxidation of the bilirubin component of the sample.

The term "rate of oxidation of bilirubin" as used herein refers to the velocity at which a bilirubin species is oxidized (i.e., loses electrons or in which its positive valence is increased). The term "standardized rate of reaction" or "standardization" as used herein refers to determining the first order rate constant for the oxidation of bilirubin in the presence of a bilirubin catalyzing reagent (e.g., a peroxidase) without albumin in the reaction mixture (i.e., in an albumin free solution) to establish a baseline rate of oxidation of bilirubin species unbound to albumin (e.g., HRP for which the Kp has been determined). The term "correction for any non-peroxidase associated reactions" as used herein refers to rectifying any errors of measurement caused by non-catalyzed oxidation of bilirubin when determining the concentration of any bilirubin species. The term "association-dissociation constant" as used herein refers to the measurement of the binding constants for the reversible association of two molecules with and from each other. As used herein, the association-dissociation constant particularly refers to the binding of bilirubin to and from albumin although one of ordinary skill in the art would recognize that association-dissociation constants of other molecules can be measured. The term "correction for the rate-limiting dissociation" as used herein refers to the rectification of error, when determining the concentration of any bilirubin species in a sample. Most such errors are caused by the dissociation or unbinding of one molecule from another (e.g., bilirubin from albumin) Preferably, the term rate-limiting dissociation refers to the velocity at which bilirubin unbinds from albumin in a sample. One of ordinary skill in the art must take the rate-limiting dissociation velocity into consideration when carrying out calculations of the instant methods as taught herein. The term "background" as used herein, refers to any unwanted rates of reactions, emissions, absorptions which contribute error into any of the measurements of the instant methods. As used herein, background measurements are made to rectify any errors in the calculations of the instant methods. The term "bilirubin oxidizing reagent" as used herein, refers to a composition which can oxidize unbound but not bound bilirubin. In a preferred embodiment such a bilirubin oxidizing reagent is a peroxide. However, one of ordinary skill in the art will realize that any oxidizing reagent which oxidizes unbound but not bound bilirubin can be used (e.g., such as potassium ferricyanide). The term "bilirubin catalyzing reagent" as used herein, refers to a composition which facilitates the oxidation of unbound but not bound bilirubin. In a preferred embodiment such a bilirubin catalyzing reagent is a peroxidase. However, any catalyzing reagent which facilitates the reaction of the oxidation of unbound bilirubin but not the oxidation of bound bilirubin can be used. The term "peroxide" as used herein, refers to a compound containing the peroxy group (—O—O—), such as, but not limited to hydrogen peroxide ($H_2O_2$). Preferably, peroxides for use in the colorimetric reactions of the instant methods are, hydrogen peroxide, t-butyl peroxide, or ethyl hydrogen peroxide. However, one of ordinary skill in the art will recognize that other acceptable peroxides suitable for use in a bilirubin assay employing colorimetric techniques are also applicable and that substitutions can be made. The term "peroxidase" as used herein, refers to any enzyme that catalyzes a reaction in which a peroxide is an electron acceptor, such as, but not limited to horseradish peroxidase (HRP). The term "diazo" as used herein, refers to any compound containing the radical, —N=N—. Virtually any diazotized aromatic amine can be used as an azo reagent in the colorimetric technique of the present method as long as the conditions taught herein have been met. Methods for forming the diazo derivatives of the above aromatic amines are well known to those in the art (Henry et al., Clinical Chemistry, Principles and Techniques, 2d. Ed., Harper and Row, New York., N.Y. (1974) pp. 1037–1079). Diazotized aromatic amines can also be stabilized by techniques well known to those in the art (Lillie, H. J. Conn's Biological Stains, Williams & Wilkins Company, Baltimore, Mass. (1969), Chap. VI). The term "diazo group" as used herein, refers to any functional group with the formula =$N_2$. The term "diazonium salts" as used herein, refers to compounds of the type R.X.N:N, where R represents an alkyl or aryl group and X represents an anion such as, but not limited to, a halide. The diazo reagents of the instant invention can be selected from, but are not restricted to, diazo derivatives of sulfanilic acid, o-dianisidine, p-chloroaniline, 1,5-dichloroaniline, 2,4-dichloroaniline, 2-methoxy-4-nitroaniline, 1aminoanthraquinonine, p-nitroanaline or 4-chloro-methylaniline. Those of ordinary skill in the art will be aware of other diazo reagents which are capable of being used in the colorimetric portion of the instant invention. The diazo reagents mentioned herein can be supplemented by any known to those in the art. The term "buffer" as used herein refers to any of the solutions described by Goode in Biochemistry, 5,467 (1996). In the method of the instant invention, bilirubin "effectors" or "promoters," as they are designated in the art, may be added during the assay. Such "effectors" or "promoters," as discussed by Henry et al., (*Clinical Chemistry Principles and Techniques*, 2d. Ed., Harper and Row, New York., N.Y. (1974) pp.1047–1048) are known for their use in bilirubin assays. Some representative effectors include, methanol, caffeine, sodium benzoate, gum arabic, salicylate, and bile salts. The precise mechanism of these effectors is not completely understood although they may serve as solubilizing reagents for the various bilirubin components. The term "animal" as used herein refers to any nonhuman living being capable of reproduction. The term "human" as used herein refers to any living non-animal. The term "heat" as used herein refers to the temperature at which the compositions of the mixtures of the instant methods are carried out. The temperature at which the instant methods are carried out is critical since velocities of reaction of the chemical reactions are temperature dependent. However, the standardization of a bilirubin catalyzing reagent, as taught herein (e.g., the standardization of the peroxidase HRP as described herein) can be performed at a variety of temperatures as long as the samples are analyzed at and the reference values are adjusted for the temperature selected. Preferably, the temperatures of the compositions of the mixtures of the instant methods are carried out at in the range of about 37° C. The term "duration of time" or defined periods of time as used herein refers to the period of time of any of the steps of the method of the instant invention. For example, the duration of time of the enzymatic reaction after adding a peroxide and peroxidase is preferably in the range of about five minutes before stopping the reaction by the addition of sulfanilic acid. More preferably in the range of about 2–10 minutes. However, those of ordinary skill in the art will recognize that it is the comparative times of reaction of the method between the reactions of the vessels that should be maintained. Therefore, those of ordinary skill in the art will realize that varying the temperature or concentrations of oxidizing reagent of the reaction can vary the time required for the reaction and those of ordinary skill will make such adjustments accordingly. Those of skill in the art will realize that variations can be made to times of reaction without straying from the intent of the methods taught herein.

The term "kit" as used herein refers to any combination of elements or interrelated parts necessary for detecting and determining the concentration of any species of bilirubin in a sample; especially those combinations of elements or interrelated parts that are necessary for detecting the presence of unbound, uuconjugated bilirubin in a sample and determining the concentration of the detected unbound, unconjugated bilirubin. One skilled in the art would realize that although the physical characteristics of the kit or its contents are not characterized, those features necessary for the formation of a kit and its physical instantiation are supplied by the teachings of the disclosure herein, the attached claims and the common knowledge concerning kits possessed by one of common skill in the art.

The instant invention may be implemented in hardware or software, or a combination of both. However, preferably, the invention is implemented in computer programs executing on programmable computers each comprising at least one processor, a data storage system (including volatile and non-volatile memory and/or storage elements), at least one input device, and at least one output device. Program code is applied to input data to perform the functions described herein and generate output information. The output information is applied to one or more output devices, in known fashion.

Each program is preferably implemented in a high level procedural or object oriented programming language to communicate with a computer system. However, the programs can be implemented in assembly or machine language, if desired. In any case, the language may be a compiled or interpreted language.

Each such computer program is preferably stored on a storage media or device (e.g., ROM or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

Utility

The methods and kit of the present invention have a variety of different uses. In addition to being used to help clinicians make decisions on the treatment of disease that is generally related to hepatic metabolisms, the methods herein may also be used by investigators conducting basic research directed to understanding bilirubin toxicity, hepatic functioning, hepatic metabolism and hepatic disease. For example, research animals whose levels of bilirubin have been experimentally altered may be monitored and tested according to the methods described herein.

EXAMPLES

The following examples are put forth so as to provide those of ordinary skill in the art with a complete disclosure and description of how to make and use the bilirubin assay described herein and are not intended to limit the scope of what the inventors regard as their invention. Efforts have been made to ensure accuracy with respect to numbers used (e.g., amounts, time, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

EXAMPLE 1

DETERMINATION OF UNBOUND BILIRUBIN BY ENZYMATIC OXIDATION

Bilirubin is rapidly oxidized by a bilirubin oxidizing reagent (e.g., ethyl hydrogen peroxide (EtOOH)) in the presence of a bilirubin catalyzing reagent (e.g., a peroxidase (e.g., horseradish peroxidase, HRP)) to nearly colorless (upon spectrophotometric analysis at 460 nm), diazo negative oxidation products. The binding of bilirubin to albumin prevents the oxidation of bilirubin. Of the total amount of bilirubin in plasma or sera, only albumin free species of bilirubin (e.g., unbound bilirubin) will oxidize under these conditions. The rate at which unbound bilirubin oxidizes is proportional to its concentration in a sample. The oxidation rate of unbound bilirubin can be measured by spectral analysis (e.g., as the rate of decrease in the optical density of sera or plasma measured at 460 nm (i.e., the wavelength at which albumin bound bilirubin has maximum absorption using a spectrophotometer)). However, the rate of oxidation of unbound bilirubin does not differentiate non-toxic conjugated bilirubin from toxic unconjugated bilirubin because both species of bilirubin are oxidized. Therefore, oxidation of unbound species of bilirubin will result in a decrease of the absorption maximum of the sample regardless of whether unbound bilirubin is conjugated.

In jaundiced newborns, the molar ratio of unconjugated bilirubin to albumin typically does not exceed 1.0. Therefore, in the clinical setting, the stoichiometry of albumin-bilirubin binding is assumed to be 1:1. The equations of mass action and equilibrium for this ratio are illustrated as:

$$B \underset{K_1}{\overset{K_{-1}}{\longrightarrow}} (a+b)$$

$$b = \frac{k_{-1}B}{k_1 a} = \frac{K_d B}{a} = \frac{B}{K_a a} \quad (2)$$

$$b \cong \frac{k_{-1}B_t}{k_1(A-B_t)} \cong \frac{K_d B_t}{(A-B_t)} \cong \frac{B_t}{K_a(A-B_t)} \quad (3)$$

Since, at clinically relevant molar ratios of bilirubin/albumin, the unbound bilirubin is a very small fraction of the total species of bilirubin, the concentration of total bilirubin ($B_t$) is substituted for the concentration of bound bilirubin (i.e., $B_t \approx B$). The concentration of non-bilirubin occupied albumin sites (a) is approximated as ($A-B_t$), where A is the total albumin. The concentration of unbound bilirubin (b) can be closely approximated from equation (3) using the concentration of total bilirubin ($B_t$) and ($A-B_t$) when $K_a$ or $K_d$ are known. The concentration of unbound bilirubin (b) can be calculated exactly by substitution of ($B_t-b$) for (b) and substitution of ($A-B_t+b$) for (a) in equation (1), to derive:

$$b = \frac{K_d(B_t-b)}{A-B_t+b} \text{ , or}$$

$$b = \frac{B_t-b}{K_a(A-B_t+b)}$$

Then, the concentration of unbound bilirubin (b) can be derived by taking the positive root of either of the following equivalent quadratic equations:

$$b^2 + (A - B_t + K_d)b - K_d B_t = 0$$

$$b = \frac{-(A-B_t+K_d) \pm \sqrt{(A-B_t+K_d)^2 + 4K_d B_t}}{2}, \quad (4)$$

or, $$K_a b^2 + (1 + K_a A - K_a B_t)b - B_t = 0$$

$$b = \frac{-(1+K_a A - K_a B_t) \pm \sqrt{(1+K_a A - K_a B_t)^2 + 4B_t K_a}}{2K_a}$$

Normally, the value of $K_d$ is approximately $10^{-2}$ µmol/liter, and typically the concentration of total bilirubin ($B_t$) is more than 5,000 times greater than the concentration of unbound bilirubin (b). Therefore, equations (3) can be substituted for equation (4) for ease of calculation without the substitution producing a significant error.

Using the peroxidase technique of the instant method, the unbound bilirubin concentration (b) can be calculated from the initial velocity of the rate of oxidation of bilirubin ($V_o$), measured as the rate of decrease in optical density measured at 460 nm) after standardized HRP (i.e., HRP in which the $K_p$ has been determined) and EtOOH are added to the sample (as in Jacobsen & Wennberg; 1974) where:

$$V_0 = -\frac{dB}{dt} = K_P[\text{HRP}] \cdot b = K_P[\text{HRP}] \cdot \frac{k_{-1} \cdot B}{k_1 \cdot a}, \quad (5)$$

after $\frac{k_{-1} \cdot B}{k_1 \cdot a}$ is substituted for $b$

However, an integrated form of equation (5) is used when combining the kinetic and colorimetric techniques into the instant method. The concentration of albumin binding sites not complexed with bilirubin ((a), or free albumin) remains constant during oxidation because the oxidation products (primarily biliverdin) also bind to the bilirubin binding sites on albumin (Ahlfors CE. Competitive interaction of biliverdin and bilirubin only at the primary bilirubin binding site on human albumin. Analytical Biochem. 110:295, 1981; incorporated by reference herein in its entirety including all figures, drawings, tables and examples). Therefore, if $B_f$ is the remaining bilirubin concentration after t minutes of reaction and $B_r$ is the initial bilirubin concentration before starting the reaction, then integration of equation No. 5 between time=zero and time=t produces:

$$\log \frac{B_f}{B_r} = Kt \quad \text{where} \quad K = \frac{K_p \cdot \text{HRP} \cdot k_{-1}}{k_1 \cdot a}$$

Multiplying each side of this equation by the actual bilirubin concentration in the reaction ( $B_r$, which is the bilirubin concentration after sample dilution by added peroxide and HRP which also dilutes (a) or the free albumin in the reaction) and dividing each side by $K_p$ HRP t will give equation (1) where the starting the unconjugated bilirubin concentration in the reaction is $B_r$:

$$\frac{B_r \cdot \log\left(\frac{B_f}{B_r}\right)}{K_p \cdot \text{HRP} \cdot t} = \frac{k_{-1} \cdot B_r}{k_1 \cdot a} = b.$$

However, dependence upon a single concentration of HRP using equation (1) can introduce serious errors when determining the value of the concentration of unbound bilirubin for the following reasons.

The rate of oxidation of unbound bilirubin is determined by the product of the value of $K_p$ and the concentration of HRP and concentration of unbound bilirubin. As unbound bilirubin is oxidized, bilirubin bound to albumin will dissociate from the binding sites on albumin and thus, replenish the pool of bilirubin which is being oxidized. Therefore, the chemical reaction of bilirubin oxidation shifts the kinetic system from a state of dynamic equilibrium to a steady state. Consequently, the enzymatic technique of the instant method is valid only if the rate at which bilirubin dissociates from albumin is substantially greater than the rate of oxidation of bilirubin (i.e., only if the rate limiting step of the reaction is not the rate of dissociation of bilirubin from albumin); otherwise the enzymatic technique will underestimate the concentration of unbound bilirubin species in the sample.

As illustrated below, if the rate at which bilirubin dissociates from albumin (i.e., rate 1) is not significantly greater (i.e., in the range of about 20 times greater) than the rate of oxidation of bilirubin (i.e., rate 2), then the enzymatic technique of the instant method underestimates the concentration of unbound bilirubin in the sample.

$$B \frac{k_{-1}}{\text{Rate 1}} > b \frac{\text{HRP} + \text{EtOOH}}{\text{Rate 2}} > \text{the formation of}$$

bilirubin oxidation products

In a solution of bilirubin and albumin, unbound bilirubin (b) is continuously added to the solution at a rate (+db/dt) and unbound bilirubin is continuously removed from the solution at a rate (−db/dt). At dynamic equilibrium, the overall change in the concentration of unbound bilirubin (b) is zero because the rates of removal and addition of unbound bilirubin cancel each other out, as demonstrated in the following equations:

$$\frac{+db}{dt} = k_{-1} \cdot B$$

$$\frac{-db}{dt} = k_1 ab$$

net $\frac{db}{dt} = k_1 B - k_1 ab = 0$, at dynamic equilibrium and, ∴

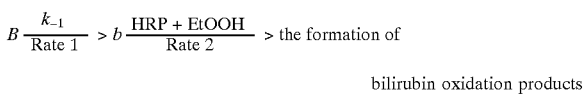

When a bilirubin oxidizing reagent (e.g., a peroxide such as EtOOH) and a bilirubin catalyzing reagent (e.g., a peroxidase such as HRP) is added to the bilirubin-albumin solution at equilibrium, the concentration of bilirubin (b) is diminished by the process of oxidation of bilirubin species that are capable of being oxidized. The dynamic equilibrium shifts to a steady state with a net decrease in both the concentration of unbound bilirubin (b) and the concentration of bound bilirubin (B) occuring over time as shown in the following equations. At steady state, $$\frac{db}{dt} \cong 0 \cong (k_{-1}B) - (k_1 ab) - (K_P[\text{HRP}]b), \text{ and}$$

$$\frac{db}{dt} \cong (k_{-1}B_t) - (k_1(A - B_t) \cdot b) - (K_P[\text{HRP}]b), \quad (6)$$

$$b_{ss} \cong \frac{K_{-1}B}{k_1 a + K_P \cdot [\text{HRP}]} \quad (7)$$

When the value of the product of the rate constant for HRP times the concentration of HRP (i.e., $K_p[\text{HRP}]$) is very small (i.e., <5.0%) compared to the association rate constant of albumin times the concentration of free albumin ($k_1(A-B_t)$) in equation (6), then the concentration of unbound bilirubin (b) will be minimally perturbed and therefore equation (7) can be reduced to equation (3) without introducing significant error into the measurement.

The following exemplar data, illustrate the teachings presented above.

| | |
|---|---|
| $B_t =$ | 10 μmol/L |
| $A =$ | 20 μmol/L |
| $k_{-1} =$ | 1/min |
| $k_1 =$ | 50 L/min · μmol |
| HRP = | 10 μg/ml |
| $K_p =$ | 18 ml/μg · min |

Substituting the above data into equation (4) the concentration of unbound bilirubin (b) in a sample can be calculated as follows:

$$b = \frac{-(10.02) - \sqrt{10.02^2 + (4.0 \cdot 0.02 \cdot 10)}}{2} = 0.0199 \, \mu\text{mol/L}$$

If the concentration of unbound bilirubin at the steady state (bss) is determined from the measurement of unbound bilirubin using a single HRP concentration (i.e., 10μg/ml) it would be approximately (bss=0.0147μmol/L) as calculated from equation (7). However, this value is in error because it underestimates the concentration of unbound bilirubin in the sample by approximately 26%.

$$b_{ss} = \frac{1 \cdot 10}{(50 \cdot 10) + (18 \cdot 10)} = 0.0147 \, \mu\text{mol/L}$$

The error results because the change in the rate of the concentration of unbound bilirubin (i.e., db/dt) is not nearly zero at the start of the reaction. Using equation (6), the change in the rate of the concentration of unbound bilirubin (db/dt) can be calculated as (10−9.95)−3.58=−3.53 μmol/L min. Thus, the concentration of unbound bilirubin (b) rapidly decreases to the steady state (bss=0.0147 μmol/L) at which db/dt approaches zero because the association-dissociation, and oxidation process of the reaction reach a steady state. Upon employing equation (6) again, the time required to reduce the concentration of bilirubin (b) to the bilirubin steady state (bss) can be calculated from the following equation as:

$$t = -\frac{1}{k_1(A-B_t) + K_P[\text{HRP}]} \log(k_{-1}B_t - k_1(A-B_t)b_{ss} + K_P[\text{HRP}]b_{ss})$$

where bss=0.0147.

Thus, the time needed to reduce the concentration of unbound bilirubin (b) to its steady state (bss) is 0.008 minutes or 0.5 seconds. Therefore, approximately 0.5 seconds are required for the concentration of unbound bilirubin (b) to decrease approximately 25% (i.e., from 0.0199 μmol/L to 0.0147 μol/L) at which time db/dt approaches zero and the bss can be calculated by employing equation (7).

Perturbations to the dynamic equilibrium concentration of the unbound bilirubin during the oxidation reaction can be minimized by using very low concentrations of HRP. However, instrument drift or background bilirubin oxidation catalyzed by hemoglobin or other oxidants in the sample may produce oxidation reaction velocities that are similar or greater in magnitude than the reaction velocities produced by the HRP catalyzed oxidation of bilirubin species at these low HRP concentrations. To prevent errors due to instrument drift or background oxidation the concentration of unbound bilirubin (b) in the sample should be measured over more than one enzymatic condition (i.e., two or more concentrations of a bilirubin oxidation catalyzing reagent such as HRP). Upon employing more than one enzymatic condition in the present technique, a linear plot can be constructed showing the relationship between the reaction velocity and the concentration of bilirubin oxidation catalyzing reagent (e.g., HRP). This data plot should have an intercept that is zero. However, if the plot of the data has a positive intercept, then it can be inferred that the rate of dissociation of bilirubin from albumin is rate limiting.

When the rate of dissociation of bilirubin from albumin is rate limiting, the concentration of unbound bilirubin (b) is calculated by either making a linear transformation of equation (7) or using a median method of analysis to analyze two equations with two unknowns (Cornish-Bowden A., Eisenthal R.; Estimation of Michaelis constant and maximum velocity from the direct linear plot. Biochem. Biophys. Acta. 523:268–272, 1978). A linear transformation of equation (7) is shown in the following equation:

$$\frac{1}{b_{ss}} = \frac{K_p}{k_{-1}B_r} \text{HRP} + \frac{k_1a}{k_{-1}B_r} \quad (8)$$

where the inverse of the intercept of the plot of the inverse of the steady state unbound bilirubin at each HRP concentration plotted against the HRP concentration, yields the equilibrium unbound bilirubin concentration.

For the median method analysis, if two HRP concentrations are used, two equations in two unknowns ($k_1$ and k1a) are generated. These two unknowns are used to calculate the equilibrium concentration of unbound bilirubin. If $bss_1$ and $bss_2$ are the steady state concentrations of unbound bilirubin at two different enzymatic concentrations (i.e., $HRP_1$ and $HRP_2$, respectively), then $$bss_1 = \frac{k_{-1}B_r}{k_1a + K_p \cdot HRP_1} \quad$$

$$bss_2 = \frac{k_{-1}B_r}{k_1a + K_p \cdot HRP_2} \quad (9)$$

and $$k_1a = \frac{bss_1 \cdot K_p \cdot HRP_1 - bss_2 \cdot K_p \cdot HRP_2}{bss_2 - bss_1} \quad (10)$$

$k_1a$ can be substituted back into one of the original equations to get $k_1$. The equilibrium concentration of unbound bilirubin is calculated using $k_1$, $k_1a$ and $B_r$:

$$b = \frac{k_{-1}B_r}{k_1a} \quad (11)$$

If more than two HRP concentrations are used, the median value of the equilibrium concentration of unbound bilirubin is calculated from all possible combinations of two equations as outlined above is taken as the dynamic equilibrium unbound bilirubin concentration (Cornish-Bowden & Eisenthal; supra).

The effect of rate limiting dissociation of albumin on the determination of the concentration of unbound bilirubin in a sample is demonstrated from the following test data.

Unbound bilirubin from the plasma from a newborn male aged three days with a total bilirubin of 20.8 mg/dL was measured using four HRP concentrations at 37° C. Data was obtained using an HP 8452 diode array spectrophotometer and monitoring the bilirubin oxidation reading at 460 mn. The overall sample dilution was 1:41.7, the $K_p$ was 16.8 per min per μg/ml HRP, ethyl hydrogen peroxide concentration was 600 μM, and the unbound bilirubin was calculated from the initial reaction velocity. The results are presented in Table 1 below.

TABLE 1

| HRP μg/ml | VELOCITY μM/min | Bss μM |
|---|---|---|
| 2.5 | 0.917 | 0.0218 |
| 5.0 | 1.666 | 0.0198 |
| 10.0 | 2.196 | 0.0131 |
| 20.0 | 3.683 | 0.0109 |

The dynamic equilibrium concentration of unbound bilirubin calculated from the linear transformation (equation (8)) is 0.0244 μM; that from a median method analysis (equations 9–11) is 0.0263 μM.

It can be seen from these data that a kinetic technique that employed only a single enzymatic concentration (e.g., an HRP concentration of 10 μg/ml) would underestimate the concentration of unbound bilirubin in the sample by approximately 50%. The instant method corrects such errors by employing very low HRP concentrations (e.g., <3 μg/ml) with much less sample dilution or by employing more than one HRP concentration. However, the kinetic test discussed above alone cannot correct for contributions to bilirubin oxidation from conjugated species of bilirubin nor for the possible errors of large sample dilution on the binding of bilirubin with albumin. Such effects and corrections are explained in the following examples.

EXAMPLE 2

DETERMINATION OF THE CONCENTRATION OF UNBOUND, UNCONJUGATED BILIRUBIN IN A SAMPLE WITH MINIMAL DILUTION BY COMBINATION OF KINETIC AND COLORIMETRIC TECHNIQUES

The following example illustrates the method to determine the concentration of unbound, unconjugated bilirubin in a biological sample. The method combines a colorimetric technique for measuring the concentrations of conjugated and total (i.e., conjugated+unconjugated) bilirubin in a sample with an enzymatic technique for measuring the concentration of unbound bilirubin in the same sample.

The method requires minimal amounts of serum or plasma (i.e., less than 0.2 ml), little sample dilution (i.e., typically less than 1:3 dilution ratio), additionally, the method eliminates interference from conjugated bilirubin in the sample, and the method can be performed rapidly using inexpensive reagents and standard laboratory equipment. The method also includes corrections for the errors produced by the rate limiting dissociation of bilirubin from albumin (as shown in Example 1) which can seriously affect the accurate determination of the value for the concentration of unbound, unconjugated bilirubin in the sample.

Reagents: Standardized horseradish peroxidase (HRP); Sigma Chemical Co. St. Louis, Mo.)) is reacted with bilirubin in albumin-free solutions and the rate constant ($K_p$) is measured using standard methods in the art. Ethyl hydrogen peroxide (EtOOH) 10–12% w/v is diluted 1:160 in a phosphate buffer. Sulfanilic acid (52 g/L) is dissolved in water containing 15 g/ml of concentrated HCL per liter. Sodium nitrite (0.5 gm) is dissolved in 100 ml of distilled water. Methanol is dissolved in water to 90% (v/v). Sample aliquots (10 µl or more) are placed in four separate vessels.

Vessel 1 is used to calculate the concentration of total bilirubin ($B_t$) and the concentration of conjugated bilirubin ($B_c$) of the sample. One volume of phosphate buffer (equal to the sample volume and equal to the volumes of HRP to be added in vessels 3 and 4) and twenty volumes of sulfanilic acid are added followed by 0.4 volume of EtOOH per of the sample volume which is used. The overall dilution of sample by added buffer (or HRP in vessels 3 and 4) and peroxide is less than 3 volumes per volume of sample. Vessel 2 is used to calculate the background oxidation of bilirubin to correct for any error resulting from non-HRP associated oxidation of bilirubin species in the sample. One volume of buffer is added to vessel 2 equal to the sample volume, then the vessel is warmed to 37° C. Next, add peroxide (0.4 volume EtOOH per sample volume) as described above. Approximately, one minute after adding peroxide, twenty volumes of sulfanilic acid are added to vessel 2 (Sulfanilic acid stops the enzymatic oxidation of bilirubin and is the initial reagent for the diazo determination of total and conjugated bilirubin).

Vessel 3 and vessel 4 are used to calculate the velocity or rate of oxidation of unbound bilirubin at two different concentrations of an enzyme which catalyzes the oxidation of bilirubin (as described in Example 1). In vessel 3, add volume of 80 µg/ml standardized HRP equal to the sample volume and warm vessel 3 to 37° C. Next, add 0.4 µL EtOOH per volume of sample volume as above. After one minute, add twenty volumes of sulfanilic acid.

In vessel 4, add volume of 160 µg/ml standardized HRP (2×the concentration of the peroxidase enzyme (HRP) as added to vessel 3) equal to the sample volume used. Warm vessel 4° to 37° C. then add 0.4 volume EtOOH per µL of sample volume (as above). After one minute, add twenty volumes of sulfanilic acid.

Following the above enzymatic procedure, any standard colorimetric measurement assay technique in the art can be used to determine the total and unconjugated amount of bilirubin present in each vessel (i.e., the 1–4 vessels above). Any diazo method common to one of ordinary skill in the art is sufficient for this assay. In the example presented herein, combine 0.05 volume of nitrite per volume of sulfanilic acid and measure the absorbance at 565 nm after one minute. This absorbance can be used to calculate the concentration of conjugated bilirubin. Subsequently, add two volumes of 90% methanol and measure the absorbance at 565 nm after two minutes. The concentration of total bilirubin is calculated using the value of this absorbance measurement. The concentration of unconjugated bilirubin is determined by subtracting the concentration value of the conjugated bilirubin from the concentration value of the total bilirubin concentration.

Analysis

After correcting for the amount of sample dilution in each vessel, the concentration of total and conjugated bilirubin can be measured from the results of measurements produced from each vessel. Subsequently, the amount of unbound unconjugated bilirubin can be calculated as follows: The steady state unbound bilirubin concentrations are calculated at each HRP concentration employed using equation (1):

$$b_{ss} = \frac{B_r \cdot \left(\log \frac{B_f}{B_r}\right)}{K_p \cdot HRP \cdot t} \; 10 \tag{1}$$

Since the conjugated bilirubin is subtracted from the total bilirubin present before calculating bss, bss equals the concentration of the steady state unconjugated, unbound bilirubin in the sample at that reaction HRP concentration (See Example 3).

If the value of bss calculated from vessel 4 is less than the value of bss of vessel 3, then the proportion of unbound bilirubin in the sample can be calculated from equation (8) or equations (9–11).

$$\frac{1}{b_{ss}} = \frac{K_p}{K_{-1}B_r} HRP + \frac{k_1 a}{K_{-1}B_r} \tag{8}$$

$$bss_1 = \frac{k_{-1}B_r}{k_1 a + K_p \cdot HRP_1} \quad bss_2 = \frac{k_{-1}B_r}{k_1 a + K_p \cdot HRP_2} \tag{9}$$

$$k_1 a = \frac{bss_1 \cdot K_p \cdot HRP_1 - bss_2 \cdot K_p \cdot HRP_2}{bss_2 - bss_1} \tag{10}$$

$$b = \frac{k_{-1}B_r}{k_1 a} \tag{11}$$

Otherwise, the unbound bilirubin concentration is the average of the two steady state determinations (the dissociation of bilirubin from albumin is not rate limiting).

Reference standards for bilirubin/albumin molar ratios at which exchange perfusion should be performed have previously been established by the applicant (Ahlfors, C.E., Criteria for exchange transfusion in jaundiced newborns. Pediatrics. 93:488, (1994); incorporated by reference herein in all its entirety including all figures, drawings, tables and examples). Reference standards for unbound bilirubin concentrations occurring at these molar ratios have been established by determining unbound unconjugated bilirubin in solutions of bilirubin in defatted albumin at the reference molar ratios. These reference values are useful for deciding whether a newborn infant with a specific unbound, unconjugated bilirubin level requires an exchange transfusion to prevent possible neurological damage.

EXAMPLE 3

MEASUREMENT OF UNBOUND UNCONJUGATED BILIRUBIN IN A SAMPLE WITH HIGH LEVELS OF CONJUGATED BILIRUBIN

The instant technology has the advantage of detecting and correcting for high levels of conjugated bilirubin in a sample in contrast to methods which only measure total unbound bilirubin. The confounding effects of the oxidation of conjugated bilirubin can lead to overestimation of the toxic unbound bilirubin fraction. The instant technology also corrects for any rate limiting dissociation of bilirubin from albumin which can lead to an underestimation of the toxic unbound bilirubin fraction. These features are illustrated in the following example demonstrating errors resulting from failing to differentiate conjugated and unconjugated unbound bilirubin in a sample and further illustrating error in determining the concentration of unbound bilirubin if only one bilirubin oxidizing concentration is employed.

Solutions:

| | | |
|---|---|---|
| Buffer: | | 0.055 M Sorensen's phosphate buffer, pH 7.4. |
| Standard: | 1. | Sigma Chemical bilirubin control (unconjugated bilirubin only): total bilirubin 19.9 mg/dL, conjugated bilirubin 0 mg/dL. |
| Sample: | 2. | ChemTrak 3 control serum with total bilirubin about 15 mg/dL and conjugated bilirubin about 4 mg/dL. |
| Kinetic: | 3. | Standardized horseradish peroxidase (HRP): 80 µg/ml and 160 µg/ml in 0.055 M Sorensen's phosphate buffer, pH 7.4. $K_P$ = 20.9 per min per µg/ml at 37° C. |
| | 4. | Ethyl hydrogen peroxide (EtOOH), 10 mM in 0.055 M Sorensen's phosphate buffer. |
| Diazo: | 5. | Sulfanilic Acid 10 g/L in 1 liter of water containing 15 ml of concentrated HCL. |
| | 6. | Sodium nitrite 0.5 g in 100 ml water. |
| | 7. | Methanol/water 90% v/v. |
| Kinetic | 1. | Sample 0.05 ml |
| Reaction: | 2. | Buffer or HRP 0.05 ml (final HRP = 36.4 and 72.8 µg/ml for the 80 and 160 µg/ml stocks, respectively). |
| | 3. | Buffer or EtOOH 0.01 ml |

HRP is added to sample in reaction vessel and warmed to 37° C. EtOOH is added and the reaction stopped after 1 min by adding 0.5 ml of sulfanilic acid. The sample solution is transferred to a cuvette and the cuvette is blanked at 566 nm in an HP 8452 spectrophotometer. Nitrite (0.025 ml) is added and the absorbance measured (566 nm) after 1 min. This absorbance value is used to calculate the concentration of conjugated bilirubin in the sample. Methanol (0.5 ml) is subsequently added and after mixing, the absorbance is again determined (566 nm) after 2 min. This second absorbance value is used to determine the concentration of total bilirubin in the sample. The concentration of unconjugated bilirubin in the sample can be determined by subtracting the value for the concentration of total bilirubin from the value for the concentration of conjugated bilirubin.

The Sigma standard is used to determine the extinction coefficient for diazo derivatives at 566 nm (reaction vessel 1). It is processed similarly to the reactions, but no bilirubin oxidizing reagent or bilirubin oxidation catalyzing reagent (e.g., EtOOH or HRP) is added. The concentrations for the total, conjugated, and unconjugated bilirubin in the ChemTrak sample are measured before and after oxidation. There was no oxidation of bilirubin by peroxide in this sample in the absence of peroxidase. The pre-oxidation bilirubin concentration is determined in the same manner as the Sigma standard (reaction tube 2). The oxidation is allowed to proceed at the two different HRP concentrations in tubes 3 and 4 for 1 minute.

REACTIONS

| | | HRP ml | | BUFFER | EtOOH |
|---|---|---|---|---|---|
| VESSEL | SAMPLE ml | 80 µg/ml | 160 µg/ml | ml | ml |
| 1 | Sigma 0.05 | — | — | 0.06 | — |
| 2 | ChemTrak 0.05 | — | — | 0.06 | — |
| 3 | ChemTrak 0.05 | 0.05 | — | — | 0.01 |
| 4 | ChemTrak 0.05 | — | 0.05 | — | 0.01 |

After 1:00 minute ( vessels' 3 and 4) 0.5 ml of sulfanilic acid +0.05 ml of nitrite followed by +0.5 ml of methanol are then added as described above.

RESULTS

| | | BILIRUBIN mg/dL | |
|---|---|---|---|
| TUBE | TOTAL | CONJUGATED | UNCONJUGATED |
| 1 | 19.9 | 0 | 19.9 (standard) |
| 2 | 15.1 | 4.2 | 10.9 |
| 3 | 12.7 | 2.0 | 10.7 |
| 4 | 11.6 | 1.1 | 10.5 |

Calculation of unbound bilirubin considering only total bilirubin concentration per (Jacobsen and Wennberg; 1974):

For HRP=36.4 µg/ml; Initial total bilirubin $(B_t)$=15.1 mg/dL; Bilirubin in reaction $(B_r)$=117.3 µM (MW for bilirubin=585 µg/µM)

$$B_r = \frac{Bt \cdot \text{sample volume}}{\text{reaction volume} \cdot 0.0585}$$

Net change in total bilirubin $(B_t f)$=12.7 mg/dL (total in Lube 3) steady state unbound bilirubin (bss) formula (see equation 1):

$$b_{ss} = -\frac{B_r \cdot \log\left(\frac{B_{tf}}{B_t}\right)}{K_P \cdot HRP \cdot \text{reaction time}}$$

Steady state unbound bilirubin=0.027 µM which is about 0.01% of the total bilirubin concentration of 15.1 mg/dL (258 µM).

For HRP-72.8, the steady state unbound bilirubin calculated as outlined above is:

$$B_t = 15.1 \text{ mg/dL}$$
$$B_r = 117.3 \text{ µM}$$
$$B_{tf} = 11.6 \text{ mg/dL}$$

and steady state unbound bilirubin=0.020 µM

Since the steady state unbound at the higher HRP is less than that at the lower HRP, dissociation of bilirubin from albumin must be rate limiting. The intercept of a plot of the reciprocal of the steady state unbound bilirubin vs. HRP gives the equilibrium unbound bilirubin which=0.042 µM.

Thus, without correcting for the rate limiting dissociation of bilirubin from albumin, the unbound bilirubin is underestimated by approximately 36%. The necessity of correcting for this problem would only become apparent when performing the test at two or more HRP concentrations. Using this example, an additional potential error occurs because no correction is made for the oxidation of conjugated as well as unconjugated bilirubin. If we subtract the conjugated bilirubin from each total bilirubin to get the unconjugated (toxic form) of bilirubin (last column in the results table), then the unconjugated unbound bilirubin is calculated as outlined above as follows where $B_r$ replaces $B_t$ and $B_f$ which replaces $B_{tf}$:

For HRP=36.4 µg/ml $B_u$=10.9 mg/dL (total unconjugated bilirubin)

$B_r$=84.7 µM $B_f$=10.7 mg/dL steady state unbound, unconjugated bilirubin=0.002 µM For HRP=72.7 µg/ml $B_u$=10.9 mg/dL (total unconjugated bilirubin)

$B_r$=84.7 µM $B_f$=10.5 mg/dL steady state unbound, unconjugated bilirubin=0.002 µM Note that since the unbound, unconjugated bilirubin is the same at each HRP the dissociation of unconjugated bilirubin from albumin is not rate limiting in this reaction. Note further, that without taking into account the interference of the conjugated bilirubin, the toxic bilirubin fraction would be mistakenly identified at a value approximately 40 times greater than its actual value. There is no indication of rate limiting dissociation of bilirubin from albumin after correcting for the interference from conjugated bilirubin. The dilution used for the determination of unconjugated unbound bilirubin in this example is 1:2.2. The advantages of the instant technology for measuring unconjugated unbound bilirubin as compared with methods that cannot differentiate conjugated and unconjugated unbound bilirubin is clear. Additionally, if only one bilirubin oxidizing reagent concentration (e.g., only one HRP concentration) is used, the concentrations of unbound bilirubin in a sample can be seriously underestimated.

EXAMPLE 4

THE EFFECT OF SAMPLE DILUTION ON MEASUREMENTS OF THE CONCENTRATION OF UNBOUND BILIRUBIN

As previously described, direct testing of bilirubin is preferred to indirect testing. However, direct testing for the concentration of unbound, unconjugated bilirubin in a sample is sensitive to the sample dilution used. The following example illustrates how large dilutions of a sample (i.e., in the range of about 1:40) in a direct test for the concentration of unbound, unconjugated bilirubin in a sample can lead to an underestimation of the true value of unbound, unconjugated bilirubin in the sample.

The drug sulfisoxazole, which displaces bilirubin from albumin, has been reported to result in the development of kernicterus when given to newborns, presumably as a consequence of increasing the concentration of unbound, unconjugated bilirubin in the blood and tissues of the neonate (Silverman WA et al Pediatrics 18:614, 1956). Using this fact, Applicant attempted to determine if altering the sample dilution in an in vitro, direct test would influence the determination of the concentration of unbound, unconjugated bilirubin. The in vitro test was employed since known concentrations of reagents could be used and the amount of unbound bilirubin in the test manipulated. Sulfisoxazole was employed, as reported by Silverman, as a means of removing bilirubin that was bound to albumin thus increasing the level of unbound, unconjugated bilirubin in the sample. It was hypothesized that these increases in the concentration of unbound, unconjugated bilirubin would be more accurately measured using the instant methods which use small sample dilutions (i.e., a dilution in the range of about 1:2) than using a direct method which required a large sample dilution (i.e., a dilution in the range of about 1:40).

Two sample dilution concentrations were used (1:1.8 and 1:41.8). The higher sample dilution (1:41.8) was chosen because it is in the range of the reported dilution required in the unbound bilirubin assay method of Jacobsen and Wennberg (Clin Chem 20:783, 1974). The lower sample dilution represents the direct assay method employed in the instant invention.

Solutions of unconjugated bilirubin in defatted albumin (total bilirubin 20 mg/dL, total albumin 3.0 g/dL) were used both with and without the presence of 15 mg/dL sulfisoxazole. This concentration of sulfisoxazole was employed since it mimicked the blood levels of sulfisoxazole reported by Silverman (i.e., 15 mg/dL).

Sulfisoxazole (0.025 ml of 6 mg/dL) or buffer (0.025 ml) was added to 0.975 ml of a 3.0 g/dL defatted albumin solution containing approximately 20 mg/dL bilirubin in 0.055M Sorrensen's buffer @ pH 7.4. Final sulfisoxazole concentration was 15 mg/dL. The peroxidase technique as described in Examples 1–3 was used to measure the unbound bilirubin concentrations at 1:1.8 and 1:41.8 dilutions using the instant method compared with the method of Jacobsen and Wennberg. A 0.1 cm path cuvette was employed to allow direct spectral analysis of the unbound bilirubin at the 1:1.8 dilution.

Methods: The 1:1.8 dilution readings were made as follows: 100 µl of bilirubin-defatted albumin sample was added to a 0.1 cm path cuvette containing 40 µl of 11 mM EtOOH and 40 µl of 16 µg/ml standardized HRP ($K_p$=19.6 ml/min µg). The HRP and EtOOH were contained in 0.055M Sorrensen's buffer, pH 7.4, but other similar buffers may be used. The final HRP concentration was 3.56 µg/ml. The fall in absorbance measured at 460 nm was monitored for more than five minutes. The concentration of unbound bilirubin was calculated from the first order change in the total bilirubin concentration after the time period using the following equation:

$$\text{Unbound bilirubin} = \frac{\log\left(\frac{\text{final absorbance at 460}}{\text{initial absorbance at 460}}\right) \cdot [\text{bilirubin}]}{5 \text{ min} \cdot [HRP] \cdot 19.6}$$

(See equation (1)). No interference from rate limiting dissociation of bilirubin from albumin was discovered when HRP concentration was approximately doubled.

Colorimetric method

10 µl each of HRP and EtOOH (in a concentration and molarity as described above) was added to 25 µl samples of bilirubin-defatted albumin solutions containing sulfisoxazole or buffer. After five minutes, 0.5 ml of a diazo reagent (sulfanilic acid+nitrite) was added to stop the reaction (the conjugated bilirubin concentration was not measured as none is present in this artificial system). Subsequently, 0.5 ml of 90% methanol was added to accelerate color formation. A similar sample containing 10 µl of buffer instead of HRP was used to determine the total bilirubin concentration at time zero (t0). The unbound bilirubin concentration was calculated using the equation (1).

The 1:41.8 dilutions were made by adding 0.025 ml of sample to 1.0 ml of buffer and starting the reaction with 10 µl each of EtOOH and HRP as above. The Jacobsen and Wennberg method was performed as above using a 1 cm path cuvette. The colorimetric technique was performed by stopping the reaction after five minutes with 1.0 ml of diazo-A and then adding 1.0 ml of 90% methanol. The results are presented in Table 1.

TABLE 1

CONCENTRATION OF UNBOUND BILIRUBIN ($\mu$m)

| Dilution | Colorimetric Method | | Spectrophotometric Method | |
|---|---|---|---|---|
| | +Sulfa | −Sulfa | +Sulfa | −Sulfa |
| 1:1.8 | 0.285 ± .003 | 0.135 ± .005 | 0.255 ± .006 | 0.110 ± .010 |
| 1:41.8 | 0.092 ± .003 | 0.098 ± .027 | 0.091 ± .003 | 0.070 ± .006 |

Values are given as the mean and standard deviation of 3 replicates.

As demonstrated in Table 1, assays employing minimal dilutions (i.e., 1:1.8) more accurately reflect the concentration of unbound, unconjugated bilirubin released by sulfisoxazole. Assays that employ higher sample dilutions (i.e., 1:40) did not detect the effect of sulfisoxazole on unbound bilirubin. Increases in the amount of unbound, unconjugated bilirubin released after applications of sulfisoxazole were approximately twofold. Such a finding is extremely significant since the toxic fraction of total bilirubin is represented within the portion that is made up of the unbound, unconjugated bilirubin species. Therefore, a method with increased sensitivity for detecting an increase in the concentration of unbound, unconjugated bilirubin will be extremely useful and advantageous. Increased sensitivity to the smallest change in the concentration of unbound, unconjugated bilirubin is beneficial since, as the binding sites of albumin for bilirubin become saturated, further small increases in total bilirubin concentration may be accompanied by disproportionately large changes in the concentration of unbound, unconjugated bilirubin which is neurotoxic. Therefore, even small increases in the concentration of total bilirubin can place a developing newborn infant at a substantial risk for developing bilirubin encephalopathy. Accordingly, an assay which is sensitive to even small increases in the amount of unbound, unconjugated bilirubin is preferred to an assay which is unable to detect elevated levels of unbound bilirubin produced by small changes in total bilirubin or by molecules capable of interfering with bilirubin-albumin binding.

In the methods described herein bilirubin from a sample can be coupled with many compounds common to one of ordinary skill in the art to form a detectable bilirubin reaction product. These methods may include but are not limited to fluorescent, radioactive, chemical, immunological, and enzymatic detection. As will be understood by one of ordinary skill in the art, many and various other modifications can be employed in forming and detecting detectable bilirubin reaction products. These are intended to be encompassed and comprehended by those of ordinary skill in the art.

In a more preferred embodiment bilirubin from a sample can be coupled with any diazotized compound common to one of ordinary skill in the art, (e.g., p-diazobenzene sulfonic acid (p-DBS)) to form a detectable colorized azobilirubin. These methods also incorporate any known or commonly used means of stabilizing diazo-compounds including but not limited to adding aromatic sulfonic acid or making fluroborate derivatives to increase and improve the stability of diazo reagents.

It will be apparent to one of ordinary skill in the art that a number of modifications may be made to the instant invention without departing from the spirit and scope of the present invention. The examples herein are not meant to be, nor should they be construed, as limiting the instant invention in any manner, shape, or form but, the examples herein are solely meant to be illustrative and to enable one of ordinary skill in the art to better embody the instant technology.

What is claimed is:

1. A method for determining the concentration of unbound, unconjugated bilirubin in a sample containing two or more bilirubin species comprising conjugated bilirubin, unconjugated bilirubin, albumin-bound bilirubin and unbound bilirubin, comprising the steps of taking a measurement of the concentration of one or more of said species in said sample by a kinetic assay and taking the measurement of the concentration of one or more of said species by a colorimetric assay and combining said measurements to determine said concentration of unbound unconjugated bilirubin.

2. The method of claim 1, wherein the kinetic assay comprises using at least two different concentrations of an enzymatic reagent.

3. The method of claim 1, wherein the kinetic assay is terminated by a reagent that can function in the colorimetric method.

4. The method of claim 3, wherein the reagent is an acid.

5. The method of claim 4, wherein the acid is sulfanilic acid.

6. The method of claim 1, wherein in the kinetic assay method the rate of dissociation of a bilirubin-albumin complex is faster than the rate of oxidation of bilirubin.

7. The method of claim 6, further comprising using at least two different concentrations of a bilirubin oxidizing reagent and a bilirubin catalyzing reagent, wherein the use of at least two bilirubin oxidizing reagent or bilirubin catalyzing reagent concentrations determines whether the rate of dissociation of a bilirubin-albumin complex is faster than the rate of oxidation of bilirubin.

8. The method of claim 7, wherein the bilirubin oxidizing reagent is a peroxide or oxygen and the bilirubin catalyzing reagent is horseradish peroxidase, bilirubin oxidase, or hemoglobin.

9. The method of claim 8, wherein the concentration of horseradish peroxidase is in the range of about 0.01 to 0.1 umol/liter.

10. The method of claim 1, wherein the sample is in a range of about equal to or greater than 10 ul in volume.

11. The method of claim 1, wherein the sample is diluted in a range of about less than 1:3.

12. The method of claim 1, comprising:
   (a) dividing a sample into four aliquots placed into four separate vessels;
   (b) with a first vessel: (i) adding a volume of buffer to said first vessel that when summed with the volume of acid added to said first vessel is less than a volume created by a dilution of the sample in a ratio in the range of about 1:3; (ii) adding a volume of acid to said first vessel sufficient to stop the enzymatic reaction of the kinetic technique in said first vessel; (iii) performing a spectral analysis on the contents of said first vessel;
   (c) with a second vessel: (i) adding a volume of buffer to said second vessel that when summed with the volume of peroxide added to said second vessel is less than a volume created by a dilution of the sample in a ratio in the range of about 1:3; (ii) heating the contents of said second vessel; (iii) adding a volume of a peroxide to said second vessel in a ratio in the range of about 0.4:1 (peroxide:sample aliquot) and after a defined period of time equal to the time period in (c)(iii), adding a volume of acid to said second vessel sufficient to stop the enzymatic reaction of the kinetic technique in said second vessel; (iv) performing a spectral analysis on the contents of said second vessel;

(d) with a third vessel: (i) adding a volume of standardized peroxidase to said third vessel that when summed with the volume of peroxide added to said third vessel is less than a volume created by a dilution of the sample in a ratio in the range of about 1:3; (ii) heating the contents of said third vessel; (iii) adding a volume of a peroxide to said third vessel in a ratio in the range of about 0.4:1 (peroxide:sample aliquot) and after a defined period of time, adding a volume of acid to said third vessel sufficient to stop the enzymatic reaction of the kinetic technique in said third vessel; (iv) performing a spectral analysis on the contents of said third vessel;

(e) with a fourth vessel: (i) adding a volume of standardized peroxidase to said fourth vessel that when summed to the volume of peroxide added to said fourth vessel is less than a volume created by a dilution of the sample in a ratio in the range of about 1:3 and wherein the concentration of the standardized peroxide is in the range of about a 50% difference than the concentration of the standardized peroxide added in (d)(i); (ii) heating the contents of said fourth vessel; (iii) adding a volume of a peroxide to said fourth vessel in a ratio in the range of about 0.4:1 (peroxide:sample aliquot) and after a defined period of time equal to the time period in (d)(iii), adding a volume of acid to said fourth vessel sufficient to stop enzymatic reaction of the kinetic technique in said fourth vessel; (iv) performing a spectral analysis on the contents of said fourth vessel 4; and (f) determining the value of the steady state concentration of unbound, unconjugated bilirubin of the sample at each peroxidase concentration used and employing these values to determine the equilibrium concentration of unbound, unconjugated bilirubin of the sample.

13. A kit for the determination of unbound, unconjugated bilirubin according to the methods of claims 1 or 12 comprising
    (a) reaction vessels;
    (b) enzymatic reagents for oxidizing unbound bilirubin, but not bound bilirubin in the presence of a bilirubin oxidizing reagent in a sample;
    (c) colorimetric reagents for determining one or more bilirubin components in a sample; and
    (d) sample containers.

14. A method of automatically determining the unbound, unconjugated bilirubin proportion of the total concentration of bilirubin in a sample, the method being implemented in a programmed computer comprising a processor, a data storage system, at least one input device, and at least one output device, the method comprising the steps of:
    (a) generating input data for the programmed computer from a spectral analyzer applied to a vessel 1, a vessel 2, a vessel 3, and a vessel 4 each prepared with a share of bilirubin from the sample, as set forth in claim 13, the input data comprising measured absorption or emission spectra for each such share;
    (b) inputting the generated input data into the programmed computer through at least one of the input devices for storage in the data storage system;
    (c) applying, to the generated input data stored in the data storage system, by means of the programmed computer, a programmed method of determining output information comprising the steady state of unbound, unconjugated bilirubin ($b_{ss}$) in reaction (n), where:

$$bss_n = \frac{B_r \cdot \log\left(\frac{Bf_n}{B_r}\right)}{K_p \cdot \text{peroxidase}_n \cdot t}$$

(1) when the peroxidase concentration of vessel 4 is greater than the peroxidase concentration of vessel 3 and $bss_4 \geq bss_3$, then the unbound unconjugated bilirubin at dymanic equilibrium is $b_{eq}=(bss_4+bss_3)/2$; and (2) if $bss_4 < bss_3$, then $b_{eq}$=the inverse of the intercept of a plot of the inverse of the values of the bilirubin of the steady state (bss) versus the value of the concentration of the peroxidase; where the linear equation is $$\frac{1}{bss_n} = \frac{K_p}{k_{-1}B_r} \cdot [\text{peroxidase}_n] + \frac{k_1 a}{k_{-1}B_r}$$

and the intercept of the slope of the plot is $$\frac{k_1 a}{k_{-1}B_r} = b_{eq};$$

or (3) if $bss_4 < bss_3$, then $b_{eq}$ is determined by median method analysis where $$bss_1 = \frac{k_{-1}B_r}{k_1 a + K_p HRP_1} \; ; \; bss_2 = \frac{k_{-1}B_r}{k_1 a + K_p HRP_2} \; ;$$

$$bss_n = \frac{k_{-1}B_r}{k_1 a + K_p HRP_n}$$

$$k_1 a = \frac{bss_1 \cdot K_p HRP_1 - bss_2 \cdot K_p HRP_2}{bss_2 - bss_1}$$

and $k_1 a$ is substituted into the initial equation to determine $k_{-1}B_r$; then $$b_{eq} = \frac{k_{-1}B_r}{k_1 a}$$

if more than two HRP concentrations are used, the median value of $b_{eq}$ is determined from all possible pairs calculated as shown above or a linear regression plot can be used to calculate $b_{eq}$
wherein:
    a=the concentration of albumin binding sites potentially available for binding by bilirubin but not currently occupied;
    $B_r$=the starting concentration of unconjugated bilirubin used in the oxidation of bilirubin (the total unconjugated bilirubin corrected for the dilution caused by the addition of a bilirubin oxidizing reagent and a bilirubin catalyzing reagent);
    $Bf_n$=the concentration of unconjugated bilirubin remaining after the oxidation of bilirubin for a period of time (t) corrected for any non-peroxidase catalyzed oxidation of bilirubin;

$b_{eq}$=b at dynamic equilibrium;

bss=b at a steady state concentration less than $b_{eq}$;

$bss_n$=bss at peroxidase concentration n (peroxidase$_n$);

$K_p$=the first order rate constant for bilirubin catalyzing reagent (e.g., HRP) catalyzed oxidation of bilirubin by a bilirubin oxidizing reagent (e.g., peroxide);

$k_{-1}$=the rate constant for the dissociation of bilirubin complexed to albumin;

$k_1$=the rate constant for the association of bilirubin with albumin to form a bound complex;

t=time (measured in minutes);

(d) applying the output information to at least one of the output devices as an indication of the proportion of unbound, unconjugated bilirubin to the total concentration of bilirubin in the sample and the equilibrium concentration of unbound bilirubin.

15. A system for automatically determining the unbound, unconjugated bilirubin proportion of the total concentration of bilirubin in a sample, the system being implemented in a programmed computer comprising a processor, a data storage system, at least one input device, and at least one output device, comprising:

(a) means for generating input data for the programmed computer from a spectral analyzer applied to a vessel 1, a vessel 2, a vessel 3, and a vessel 4 each prepared with a share of bilirubin from the sample, as set forth in claim 13, the input data comprising measured absorption or emission spectra for each such share;

(b) means for inputting the generated input data into the programmed computer through at least one of the input devices for storage in the data storage system;

(c) applying, to the generated input data stored in the data storage system, by means of the programmed computer, a programmed method of determining output information comprising the steady state of unbound, unconjugated bilirubin ($b_{eq}$), where:

(1) when the peroxidase concentration of vessel 4 is greater than the peroxidase concentration of vessel 3 and $bss_4 \geq bss_3$, then $b_{eq}$=($bss_4$+$bss_3$)/2; and (2) if $bss_4$<$bss_3$, then $b_{eq}$=the inverse of the intercept of a plot of the inverse of the values of the bilirubin of the steady state (bss) versus the value of the concentration of the peroxidase;

where the linear equation is $$\frac{1}{bss_n} = \frac{K_p}{k_{-1}B_r} \cdot [\text{peroxidase}_n] + \frac{k_1 a}{k_{-1}B_r}$$

and the intercept of the slope of the plot is $$\frac{k_1 a}{k_{-1}B_r} = b_{eq};$$

or (3) if $bss_4$<$bss_3$, then $b_{eq}$ is determined by median method analysis where $$bss_1 = \frac{k_{-1}B_r}{k_1 a + K_p HRP_1} \; ; \; bss_2 = \frac{k_{-1}B_r}{k_1 a + K_p HRP_2} \; ;$$

$$bss_n = \frac{k_{-1}B_r}{k_1 a + K_p HRP_n}$$

$$k_1 a = \frac{bss_1 \cdot K_p HRP_1 - bss_2 \cdot K_p HRP_2}{bss_2 - bss_1}$$

and $k_1 a$ is substituted into the initial equation to determine $k_{-1}B_r$; then $$b_{eq} = \frac{k_{-1}B_r}{k_1 a}$$

if more than two HRP concentrations are used, the median value of $b_{eq}$ is determined from all possible pairs calculated as shown above or a liner regression plot can be used to calculate $b_{eq}$ wherein:

$K_p$=the rate constant for the oxidation of bilirubin;

$B_1$=total concentration of bilirubin of the share in vessel 1 minus the conjugated proportion of bilirubin measured from vessel 1;

$k_1$=the rate association constant for albumin in bilirubin $k_{-1}$=the rate constant of the dissociation of bilirubin from albumin a=the concentration of unbound albumin $B_r$=the starting concentration of unconjugated bilirubin used in the oxidation of bilirubin (the total unconjugated bilirubin corrected for the dilution caused by the addition of a bilirubin oxidizing reagent and a bilirubin catalyzing reagent);

$B_2$=total concentration of bilirubin of the share in vessel 2 minus the conjugated proportion of bilirubin measured from vessel 2;

$B_b$=background oxidation=$B_1$–$B_2$;

$B_3$=total concentration of bilirubin of the share in vessel 3 minus the conjugated concentration of bilirubin measured from vessel 3 plus $B_b$;

$B_4$=total concentration of bilirubin of the share in vessel 4 minus the conjugated concentration of bilirubin measured from vessel 4 plus $B_b$;

t=time of reaction;

peroxidase$_3$=the concentration of peroxidase in vessel 3;

peroxidase$_4$=the concentration of peroxidase in vessel 3; and $$bss_3 = \frac{\log(B_3 + B_b/B_1) \cdot B_r}{K_p[\text{peroxidase}_3] \cdot t} \; ; \; bss_4 = \frac{\log(B_4 + B_b/B_1) \cdot B_r}{K_p[\text{peroxidase}_4] \cdot t}$$

(d) applying the output information to at least one of the output devices as an indication of the proportion of unbound, unconjugated bilirubin to the total concentration of bilirubin in the sample and the equilibrium concentration of unbound bilirubin.

16. A computer program, residing on a computer-readable medium, for automatically determining the unbound, unconjugated bilirubin proportion of the total concentration of bilirubin in a sample, comprising instructions for causing a computer:

(a) receive input data from a spectral analyzer applied to a vessel 1, a vessel 2, a vessel 3, and a vessel 4 each prepared with a share of bilirubin from the sample, as set forth in claim 13, the input data comprising measured absorption or emission spectra for each such share;

(b) computing the steady state ($bss_x$) of unbound, unconjugated bilirubin, where:

(1) when the peroxidase concentration of vessel 4 is greater than the peroxidase concentration of vessel 3 and $bss_4 \geq bss_3$, then $b_{eq}=(bss_4+bss_3)/2$; and (2) if $bss_4 < bss_3$, then $b_{eq}$=the inverse of the intercept of a plot of the inverse of the values of the bilirubin of the steady state (bss) versus the value of the concentration of the peroxidase;

where the linear equation is $$\frac{1}{b_{ss}} = \frac{K_p}{k_{-1}B_r} \cdot [\text{peroxidase}] + \frac{k_1 a}{k_{-1}B_r}$$

and the intercept of the slope of the plot is $$\frac{k_1 a}{k_{-1}B_r} = b_{eq}$$

where $b_{eq}$=the dynamic equilibrium unbound bilirubin wherein:

$K_p$=the rate constant for the oxidation of bilirubin;

$B_1$=total concentration of bilirubin of the share in vessel 1 minus the conjugated proportion of bilirubin measured from vessel 1;

$k_1$=the rate association constant for albumin in bilirubin $k_{-1}$=the rate constant of the dissociation of bilirubin from albumin a=the concentration of unbound albumin $B_r$=the concentration of unconjugated bilirubin in the reaction vessel where $B_r=(B_1 \cdot \text{sample volume}) \div (\text{sum of the volumes of \{Peroxidase+Peroxide+Sample\}})$ $B_2$=total concentration of bilirubin of the share in vessel 2 minus the conjugated proportion of bilirubin measured from vessel 2;

$B_b$=background oxidation=$B_1-B_2$;

$B_3$=total concentration of bilirubin of the share in vessel 3 minus the conjugated concentration of bilirubin measured from vessel 3 plus $B_b$;

$B_4$=total concentration of bilirubin of the share in vessel 4 minus the conjugated concentration of bilirubin measured from vessel 4 plus $B_b$;

t=time of reaction;

$\text{peroxidase}_3$=the concentration of peroxidase in vessel 3;

$\text{peroxidase}_4$=the concentration of peroxidase in vessel 3; and $$bss_3 = \frac{\log(B_3 + B_b/B_1) \cdot B_r}{K_p[\text{peroxidase}_3] \cdot t} \; ; \; bss_4 = \frac{\log(B_4 + B_b/B_1) \cdot B_r}{K_p[\text{peroxidase}_4] \cdot t}$$

(c) applying the output information to at least one of the output devices as an indication of the proportion of unbound, unconjugated bilirubin to the total concentration of bilirubin in the sample and the equilibrium concentration of unbound bilirubin.

17. A system for automatically determining the unbound, unconjugated bilirubin proportion of the total concentration of bilirubin in a sample, the system being implemented in a programmed computer comprising a processor, a data storage system, at least one input device, and at least one output device, comprising:

(a) means for generating input data for the programmed computer from a spectral analyzer applied to a vessel 1, a vessel 2, a vessel 3, and a vessel 4 each prepared with a share of bilirubin from the sample, as set forth in claim 13, the input data comprising measured absorption or emission spectra for each such share;

(b) means for inputting the generated input data into the programmed computer through at least one of the input devices for storage in the data storage system;

(c) applying, to the generated input data stored in the data storage system, by means of the programmed computer, a programmed method of determining output information comprising the steady state of unbound, unconjugated bilirubin ($b_{eq}$), where:

(1) when the peroxidase concentration of vessel 4 is greater than the peroxidase concentration of vessel 3 and $bss_4 \geq bss_3$, then $b_{eq}=(bss_4+bss_3)/2$; and $$\text{if } bss_4 < \frac{1}{b_{ss}} = \frac{K_P}{k_{-1}B_r} [HRP] bss_3, \quad (2)$$

then $b_{eq}$=the inverse of the intercept of a plot of the inverse of the values of the bilirubin of the steady state (bss) versus the value of the concentration of the peroxidase;

where the linear equation is $$\frac{1}{b_{ss}} = \frac{K_P}{k_{-1}B_r} \cdot [\text{peroxidase}] + \frac{k_1 a}{k_{-1}B_r}$$

and the intercept of the slope of the plot is $$\frac{k_1 a}{k_{-1}B_r} = b_{eq}$$

where $b_{eq}$=the dynamic equilibrium unbound bilirubin wherein:

$K_p$=the rate constant for the oxidation of bilirubin;

$B_1$=total concentration of bilirubin of the share in vessel 1 minus the conjugated proportion of bilirubin measured from vessel 1;

$k_1$=the rate association constant for albumin in bilirubin $k_{-1}$=the rate constant of the dissociation of bilirubin from albumin a=the concentration of unbound albumin $B_r$=the concentration of unconjugated bilirubin in the reaction vessel where $B_r=(B_1 \cdot \text{sample volume}) \div (\text{sum of the volumes of \{Peroxidase+Peroxide+Sample\}})$ $B_2$=total concentration of bilirubin of the share in vessel 2 minus the conjugated proportion of bilirubin measured from vessel 2;

$B_b$=background oxidation=$B_1-B_2$;

$B_3$=total concentration of bilirubin of the share in vessel 3 minus the conjugated concentration of bilirubin measured from vessel 3 plus $B_b$;

$B_4$=total concentration of bilirubin of the share in vessel 4 minus the conjugated concentration of bilirubin measured from vessel 4 plus $B_b$;

t=time of reaction;

peroxidase$_3$=the concentration of peroxidase in vessel 3;

peroxidase$_4$=the concentration of peroxidase in vessel 3; and $$bss_3 = \frac{\log(B_3 + B_b/B_1) \cdot B_r}{K_p[\text{peroxidase}_3] \cdot t} \; ; \; bss_4 = \frac{\log(B_4 + B_b/B_1) \cdot B_r}{K_p[\text{peroxidase}_4] \cdot t}$$

(d) applying the output information to at least one of the output devices as an indication of the proportion of unbound, unconjugated bilirubin to the total concentration of bilirubin in the sample and the equilibrium concentration of unbound bilirubin.

18. The method according to claim 1, wherein the kinetic assay measures the rate of oxidation of unbound bilirubin by a bilirubin oxidizing reagent in the presence of a catalyzing reagent which oxidizes unbound bilirubin but not bound bilirubin.

19. The method according to claim 1 wherein the colorimetric assay measures the concentration of both conjugated and total bilirubin in the sample.

20. The method according to claim 1 wherein the colorimetric assay measures the concentration of both conjugated and total bilirubin in the sample, and the kinetic assay measures the rate of oxidation of unbound bilirubin by a bilirubin oxidizing reagent in the presence of a catalyzing reagent which oxidizes unbound bilirubin but not bound bilirubin.

* * * * *

UNITED STATES PATENT AND TRADEMARK OFFICE
CERTIFICATE OF CORRECTION

PATENT NO. : 5,804,405
DATED : September 8, 1998
INVENTOR(S) : Charles E. Ahlfors It is certified that error appears in the above-identified patent and that said Letters Patent is hereby corrected as shown below:

On the title page: Item [57] Abstract, line 13

"$B^c$" should read --Bc--

Column 17, Line 16: "µol/L" should read --µmol/L--

Column 18, Line 11: "K" should read --$K_1$--

Column 18, Line 27: "mn" should read --nm--

Column 19, Line 53 and 54: "0.4 µL EtOOH per volume of sample volume"

should read --0.4 volume EtOOH per sample--

Column 19, Line 57: "2xthe" should read --2x the--

Column 19, Line 59: "per µL of sample" should read --per sample--

Column 20, Line 4: "two" should read --twenty--

Signed and Sealed this

Ninth Day of January, 2001

Attest:

Q. TODD DICKINSON

*Attesting Officer*    *Commissioner of Patents and Trademarks*